United States Patent [19]
Dobkin et al.

[11] Patent Number: 5,514,781
[45] Date of Patent: May 7, 1996

[54] USE OF AZOLES AS VIRUCIDAL AGENTS IN SOLUTIONS OF BIOLOGICALLY ACTIVE PROTEINS

[75] Inventors: Milton B. Dobkin; Paul Ng, both of Lafayette; George B. Dove, Danville, all of Calif.

[73] Assignee: Bayer Corporation, Berkeley, Calif.

[21] Appl. No.: 226,593

[22] Filed: Apr. 11, 1994

[51] Int. Cl.$^6$ .................. C07K 16/00; C07K 14/745; C07K 14/75; C07K 14/755

[52] U.S. Cl. .................. 530/390.1; 530/381; 530/382; 530/383; 548/335.1; 548/339.1; 548/335.5; 548/317.1

[58] Field of Search .................. 530/381, 382, 530/390.1, 383; 548/335.1, 339.1, 335.5, 317.1

[56] References Cited

U.S. PATENT DOCUMENTS 4,661,493  4/1987  Gibbs .................. 514/252

OTHER PUBLICATIONS

Waldmann, Science, vol. 252, pp. 1657–1662 (1991).

Mitra et al., Curr Stud Hematol Blood Transfus., No. 56, pp. 34–43 (1989).

Lembach et al., Curr Stud Hematol Blood Transfus. No. 56, pp. 97–108 (1989).

Docherty et al., Antimicroh. Agents Chemother. vol. 31(10), pp. 1562–1566 (1987).

Murata et al., Agr. Biol. Chem., vol. 38 (2), pp. 477–478 (1974).

Seaver, Genetic Engineering News, pp. 10 and 21, (1994).

Primary Examiner—Christina Y. Chan
Attorney, Agent, or Firm—James A. Giblin

[57] ABSTRACT

Soluble azoles in aqueous solutions can be used as virucidal agents for biologically active protein preparations.

6 Claims, No Drawings

USE OF AZOLES AS VIRUCIDAL AGENTS IN SOLUTIONS OF BIOLOGICALLY ACTIVE PROTEINS

BACKGROUND OF THE INVENTION

1. Field:

This disclosure is concerned generally with methods of inactivating viruses in solutions of biologically active proteins and, specifically, with the use of azoles to inactivate viruses in an aqueous solution of biologically active therapeutic proteins.

2. Prior Art:

The importance of eliminating viral infectivity in therapeutic products has long been recognized. This is especially true in the case of biologically active products derived from human blood or, more recently, from cell cultures used to make products of biotechnology (e.g., recombinant DNA products and monoclonal antibodies).

In considering virucidal agents for biologically active proteins, the primary goals are to assure complete virucidal action while not adversely affecting the biological activity of the protein. These goals require consideration of such variables as the protein itself, the nature of its activity and/or activity site, the virucidal agent, the importance and/or ease of its removal after use, and variables of the treatment itself, such as time, temperature and concentration.

Heat treatment alone can be used for virucidal treatment of some proteins (e.g., pasteurization at 60° C.). However, it is difficult in many cases to avoid loss of biological activity or utility when heat alone is used.

To avoid some of the disadvantages or activity losses resulting from the use of heat alone, various chemical agents have been used or proposed as virucidal agents for biologically active proteins. See, for example, U.S. Pat. No. 5,071,650, to G. Dove, M. Dobkin and M. Shearer, disclosing the use of alcohols under specific conditions.

The utility of nonexplosive organic solvent/detergent mixtures for the preparation of viral vaccines, and, more recently, for inactivation of endogenous viruses in preparations of biological products derived from human plasma, have been limited by conditions of use (e.g., pH). One virucidal compound used with biologically active proteins at neutral pH is tri-n-butyl phosphate (TNBP). See, for example, U.S. Pat. No. 4,540,573 to A. Neurath and B. Horowitz, disclosing the use of TNBP to inactivate lipid-enveloped viruses. See also U.S. Pat. No. 5,110,910 to G. Tsay disclosing the use of TNBP as a virucide under controlled pH, conductivity and protein concentration. Unfortunately, current virucides typically inactivate mainly lipid-enveloped viruses and have not been shown to be effective against a hardier class of viruses which lack lipid envelopes.

Various azole compounds have been used as fungicides (e.g., see U.S. Pat. No. 5,006,513 to Hector, et al.), but we are unaware of any suggestion to use them as virucides in solutions of biologically active proteins, especially against non-lipid containing viruses. We now have found that azoles provide a unique ability to inactivate both enveloped and non-enveloped viruses in aqueous solutions while preserving the biological activity of proteins such as immunoglobulins. Details of our method are described below.

SUMMARY OF THE INVENTION

Our method of inactivating both enveloped and non-enveloped viruses in an aqueous solution of biologically active, therapeutic proteins comprises contacting the solution with an azole, under conditions sufficient to assure the substantial reduction of both classes of viruses (2 or more logs virus titer reduction for each class) without adversely affecting the biological activity of the proteins (i.e., greater than 50% recovery of activity). Virucidal activity may be enhanced by the presence of detergents. The primary functional group responsible for inactivation is the pentameric azole ring, which may be modulated by changes to the ring or by additional functional groups attached to the ring. A preferred azole is imidazole, preferably used with a detergent as described below.

SPECIFIC EMBODIMENTS

Azoles have been found to demonstrate virucidal activity with both enveloped and non-enveloped viruses, as illustrated below. As used herein, the terms azole or azole analogs or azole derivatives refer to compounds having a pentameric azole ring and which have virucidal activity under conditions of temperature, pH and concentration which do not adversely affect the biological activity of a protein of interest such as a therapeutic protein.

MATERIALS AND METHODS

Chemical Agents

Azoles used were: imidazole, alpha-amino-1H-imidazole-4-propanoic acid (histidine), 2-imidazolidinone (ethylene urea), 1H-imidazole4-ethanamine (I4EA). Azoles, detergents (e.g., polysorbate 80, TRITON X-100), and buffer salts were reagent grade and obtained from Sigma Chemicals, St. Louis, Mo. Polysorbate 80 is an oleate ester of sorbitol and its anhydrides copolymerized with approximately 20 moles of ethylene oxide for each mole of sorbitol and sorbitol anhydrides. Triton X-100 is a trademark for octoxynol.

Virus

Enveloped:

Vesicular stomatitis virus (VSV), Indiana strain, obtained from the Finnish Red Cross, is a Rhabdovirus (RNA). Vaccinia virus, Lederle strain, ATCC VR-118, is a Poxvirus (DNA). Sindbis is a Togavirus (RNA). Herpes simplex virus type 1 (HSV-1) is a Herpesvirus (DNA).

Non-enveloped:

Encephalomyocarditis virus (EMC) is a murine picornavirus (RNA). Poliovirus type 2 is a human picornavirus (RNA). Reovirus type 3 virus is a reovirus (RNA). Derivation of viruses was reported previously (see, Lembach, et al., *Current Studies in Hematology and Blood Transfusion.* Basel, Karger, 1989; 56:97–108).

Virus Assay

All viruses except Sindbis were titrated under standard conditions on monolayers of VERO cells grown in 24 well plates using 4 wells per dilution. Titers are expressed in terms of tissue culture infectious doses as a 50% end-point per mL ($TCID_{50}$/mL). Sindbis virus was titrated in similar fashion on monolayers of BHK-21 cells under standard conditions assessing cytopathic effects.

Proteins

Factor VIII (FVIII), one of the coagulation factors administered to hemophiliacs, was derived from recombinant baby hamster kidney cells grown in suspension culture. This recombinant FVIII product (rFVIII) is described in EP 160,457 in the name of D. J. Capon, et al.

Monoclonal antibodies (human) of class G (m-IgG, antitumor necrosis factor, cell line ATCC Accession No. HB9736), were derived from Epstein-Barr virus-transformed human B lymphocytes grown in suspension culture. IgG was purified to greater than 98% by ion exchange and size exclusion chromatography. These antibodies are described in EP 351,789 in the name of H. Kuo.

Fibrinogen was purified from human plasma by the Cohn-Oncley process. Human serum albumin was purified from human plasma by the Cohn-Oncley process (Fraction V). See, for example, Cohn, E. J., L. E. Strong, W. L. Hughes, D. J. Mulford, J. N. Ashworth, M. Melin and H. L. Taylor. "Preparation and Properties of Serum and Plasma Proteins. IV. A System for the Separation into Fractions of the Protein and Lipoprotein Components of Biological Tissues and Fluids." J. Am. Chem. Soc. 68, 459 (1946).

Protein recovery was evaluated by A280, radial immunodiffusion, and FPLC-SUPEROSE 6 (Pharmacia fast protein liquid chromatography by size exclusion). FVIII was assayed by a modified method of Langdell (Langdell, R. D., Wagner, R. H., Brinkhouse, A. "Effect of anti-hemophiliac Factor on One-Stage clotting Test," J. Lab. Clin. Med. 41: 637–647, 1953) based on activated partial thromboplastin time (APTT).

Treatment Protocol

Protein solutions were seeded with a 1/100 dilution of stock virus to minimize the effects of virus-containing medium. A volume of azole solution was added to give a final desired concentration. Treated and control samples were incubated with intermittent gentle mixing under the specified conditions (time, temperature). Samples were removed at appropriate intervals and titrated immediately for residual infectious virus.

RESULTS

Studies were conducted to determine the types of azoles exhibiting virucidal activity. As seen in Table 1, a wide variety of azoles are effective in reducing VSV titer. The primary functional group resulting in virus inactivation is the pentameric azole ring, which may be modulated by changes to the ring or by additional functional groups attached to the ring.

TABLE 1

Inactivation Kinetics of VSV in FVIII containing a variety of azoles at 40° C.

| Azole Concentration Time (hrs) | Imidazole 0.02M | Imidazole 0.2M | Histidine 0.2M | 2-Imidazolidinone 0.2M | I4EA 0.2M |
|---|---|---|---|---|---|
| | Virus Titer Remaining | | | | |
| 0 | (7.5*) | (7.75) | (8.25) | (7.75) | (8.25) |
| 1 | — | 6.25 | 7.0 | >7.5 | 7.25 |
| 3 | — | 3.75 | 4.5 | 7.0 | 5.5 |
| 4 | — | 2.5 | 3.0 | 5.75 | 5.0 |
| 5 | — | <1.5 | 2.5 | 5.75 | 4.25 |
| 6 | 5.75 | <1.5 | 2.75 | 5.25 | 3.5 |

( ): untreated
*: $LOG_{10}TCID_{50}/ML$
—: not tested

Studies were conducted to determine the types of viruses susceptible to inactivation by azoles. Table 2 lists conditions necessary to provide substantial virus reduction (2 or more logs reduction) for a variety of enveloped and non-enveloped viruses.

TABLE 2

Inactivation Parameters for a Variety of Enveloped and Non-Enveloped Viruses in FVIII.

| | Enveloped Viruses | | | | Non-Enveloped Viruses | | |
|---|---|---|---|---|---|---|---|
| Virus | VSV | HSV-1 | Sindbis | Vaccinia | Polio-2 | EMC | REO-3 |
| Treatment Time (hr) | 0.25 | 0.25 | <1 | <1 | 7 | 4 | 7 |
| Temperature (C.) | 15 | 15 | 15 | 40 | 40 | 40 | 40 |
| Imidazole (M) | 0.02 | 0.02 | 0.02 | 0.2 | 0.2 | 0.2 | 0.2 |
| TRITON X-100 (%) | 0.05 | 0.05 | 0.05 | 0.1 | 0.1 | 0.1 | 0.1 |
| Titer (initial) | 8.0* | 6.75 | 8.25 | 6.25 | 6.5 | 6.5 | 7.75 |
| Titer (final) | <1.5 | <1.5 | <1.5 | <1.5 | 4.5 | 1.5 | 4.25 |
| Reduction | >6.5 | >5.25 | >6.75 | >4.75 | 2.0 | 5.0 | 3.5 |

*: $LOG_{10}TCID_{50}/ML$

Detergents may enhance virucidal activity. Table 3 lists several examples, demonstrating specific conditions of increased activity or lack thereof.

TABLE 3

Effect of Detergents and Temperature on Virucidal Activity of Imidazole.

| Virus | Sindbis | | EMC | | |
|---|---|---|---|---|---|
| Temperature (C.) | 15 | | 15 | | 40 |
| Imidazole Conc'n. (M) | 0.02 | | 0.2 | | 0.2 |
| TRITON X-100 Conc'n. (%) | none | 0.05 | none | 0.1 | none |
| Time (hr) | Virus Titer Remaining | | | | |
| 0 | 8.25* | 8.25* | 6.5 | 6.5 | 6.5 |
| 0.5 | — | 2.0 | — | 6.0 | 5.7 |
| 1 | 8.0 | <1.5 | 6.25 | 5.75 | 5.7 |
| 2 | | | 5.75 | 6.25 | 3.25 |
| 5 | | | 6.25 | 6.25 | <1.5 |

*: $LOG_{10}TCID_{50}/ML$
—: not tested

A variety of proteins in aqueous solutions are not substantially affected by treatment with azoles. Recovery may vary, depending on the protein. For example, FVIII is a very large, labile protein. Conditions permitting substantial virus inactivation without loss of activity are uncommon. Table 4 defines kinetics for FVIII.

TABLE 4

Protein Recovery in the Presence of Imidazole Under a Variety of Conditions.

| Protein | FVIII | FVIII | FVIII | IgG | Fibrinogen |
|---|---|---|---|---|---|
| Imidazole Concentration (M) | 0.02 | 0.2 | 0.2 | 0.5 | 0.2 |
| Temperature (C.) | 40 | 30 | 40 | 40 | 40 |
| Time | Protein Recovery (% of initial) | | | | |
| 0 | 100 | 100 | 100 | 100 | 100 |
| 1 | | 91 | 85 | | |
| 2 | | | 92 | | |
| 3 | | 83 | 86 | | |
| 4 | | 83 | 79 | | |
| 5 | | 84 | 78 | | |
| 6 | | 86 | 77 | | |
| 7 | >95 | 81 | 75 | | |
| 24 | >95 | | | >95 | >95 |

DISCUSSION

Speculation on how imidazole works is as follows:

Each virion consists of a protein coat which has many clusters of protein subunits. Subunits are stabilized in solution by metal ions and may dissociate when the metal concentration is reduced. The binding of protein subunits to metal ions is facilitated by the electron-donating side chains of residues such as histidine. A complex is formed between a metal ion and the epsilon nitrogen from the imidazole ring of a histidine residue on the protein. In virus-containing solution, free imidazole competes with the imidazole on the protein subunits. As metal ions bind to the free imidazole, the protein subunits become unstable and the virus coat is opened, thereby destroying the native structure of the virion. The phenomenon is also dependent on the concentration of protein (e.g., FVIII) in solution, further supporting that imidazole in solution competes with the imidazole on the protein.

Given the above disclosure it is thought variations will occur to those skilled in the art. Thus, the above examples should be construed as illustrative and the invention disclosed here should be limited only by the following claims.

We claim:

1. A method of inactivating both enveloped and non-enveloped viruses in an aqueous solution of therapeutic, biologically active proteins selected from the group consisting of coagulation factors and antibodies comprising the step of contacting the solution with an azole selecting from the group consisting of imidazole, histidine, 2-imidazolidinone, and 1H-imidazole-4-ethanamine under conditions sufficient to result in a reduction of at least 2 logs virus titer and recovery of greater than 50% of biological activity of the proteins.

2. The method of claim 1 wherein the azole is imidazole.

3. The method of claim 1 comprising the additional steps of including a detergent selected from polysorbate 80 and octoxynol.

4. The method of claim 3 wherein the detergent is Octoxynol.

5. The method of claim 1 wherein the biologically active protein is Factor VIII.

6. The method of claim 1 wherein the biologically active protein is fibrinogen.

* * * * *